US012324866B2

(12) United States Patent
Pellikaan et al.

(10) Patent No.: US 12,324,866 B2
(45) Date of Patent: Jun. 10, 2025

(54) METHOD FOR PREPARING A TISSUE-ADHESIVE SHEET

(71) Applicant: GATT TECHNOLOGIES B.V., Nijmegen (NL)

(72) Inventors: Hubert Clemens Pellikaan, Utrecht (NL); Abraham Reinier Keereweer, Nijmegen (NL); Johannes Caspar Mathias Elizabeth Bender, Nijmegen (NL)

(73) Assignee: GATT Technologies B.V., Nijmegen (NL)

( * ) Notice: Subject to any disclaimer, the term of this patent is extended or adjusted under 35 U.S.C. 154(b) by 649 days.

(21) Appl. No.: 17/573,541

(22) Filed: Jan. 11, 2022

(65) Prior Publication Data

US 2022/0133948 A1  May 5, 2022

Related U.S. Application Data

(63) Continuation of application No. PCT/EP2020/069445, filed on Jul. 9, 2020.

(30) Foreign Application Priority Data

Jul. 12, 2019 (EP) .................................... 19186041

(51) Int. Cl.
| | | |
|---|---|---|
| *A61L 24/00* | (2006.01) | |
| *D06M 10/00* | (2006.01) | |
| *D06M 10/10* | (2006.01) | |
| *D06M 15/356* | (2006.01) | |
| *D06M 15/53* | (2006.01) | |
| *D06M 15/564* | (2006.01) | |
| *D06M 23/08* | (2006.01) | |
| *D06M 23/14* | (2006.01) | |

(52) U.S. Cl.
CPC ....... *A61L 24/0094* (2013.01); *A61L 24/0042* (2013.01); *D06M 10/00* (2013.01); *D06M 10/10* (2013.01); *D06M 15/3562* (2013.01); *D06M 15/53* (2013.01); *D06M 15/564* (2013.01); *D06M 23/08* (2013.01); *D06M 23/14* (2013.01); *A61L 2400/04* (2013.01)

(58) Field of Classification Search
CPC ............ A61L 24/0094; A61L 24/0042; D06M 10/00; D06M 10/10; D06M 15/3562; D06M 15/53; D06M 15/564; D06M 23/08; D06M 23/14
See application file for complete search history.

(56) References Cited

U.S. PATENT DOCUMENTS

| | | | |
|---|---|---|---|
| 6,733,845 B1 * | 5/2004 | Caramaro | B29B 15/105 427/482 |
| 7,435,425 B2 | 10/2008 | Qian et al. | |
| 8,545,871 B2 | 10/2013 | Arthur et al. | |
| 8,815,832 B2 | 8/2014 | Wang et al. | |
| 2003/0064109 A1 | 4/2003 | Qian et al. | |
| 2006/0062768 A1 | 3/2006 | Hnojewyj | |
| 2008/0312315 A1 | 12/2008 | Daniloff et al. | |
| 2010/0233246 A1 | 9/2010 | Sehl et al. | |
| 2011/0045034 A1 | 2/2011 | Nur et al. | |
| 2011/0250257 A1 | 10/2011 | Arthur et al. | |
| 2011/0251574 A1 | 10/2011 | Hedrich et al. | |
| 2012/0021058 A1 | 1/2012 | Goessl | |
| 2013/0096063 A1 | 4/2013 | Hedrich et al. | |
| 2013/0129710 A1 | 5/2013 | Nordhaus et al. | |
| 2013/0316974 A1 | 11/2013 | Wang et al. | |
| 2013/0337036 A1 | 12/2013 | Arthur et al. | |
| 2014/0336147 A1 | 11/2014 | Berman et al. | |
| 2015/0010612 A1 * | 1/2015 | Vogt ........................ | A61L 24/08 424/678 |
| 2015/0045507 A1 | 2/2015 | Bender et al. | |
| 2015/0151020 A1 | 6/2015 | Kageyama et al. | |

(Continued)

FOREIGN PATENT DOCUMENTS

| | | |
|---|---|---|
| CN | 1273862 A | 11/2000 |
| CN | 101594890 A | 12/2009 |

(Continued)

OTHER PUBLICATIONS

Boerman et al., "Next Generation Hemostatic Materials Based on NHS-Ester Functionalized Poly(2-oxazoline)s", Biomacromolecules, vol. 18, No. 8, Jul. 12, 2017, pp. 2529-2538.
International Search Report and Written Opinion for PCT Appl. Ser. No. PCT/EP2020/069445 dated Sep. 30, 2020 (7 pages).
Lewis et al., "Control of bleeding in surgical procedures: critical appraisal of Hemopatch (Sealing Hemostat)", Dove Press Journal, Medical Devices: Evidence and Research 2016, vol. 9, Dec. 22, 2015, pp. 1-10.
Schuhmacher et al., "Safety and effectiveness of a synthetic hemostatic patch for intraoperative soft tissue bleeding", Dove Press Journal, Medical Devices: Evidence and Research 2015, vol. 8, Mar. 31, 2015, pp. 167-174.
Southmedic, "Gelita Medical Hemostatic Agent products available from Southmedic", 6-page brochure for Gelita Tuft-It, copyright 2024.

(Continued)

*Primary Examiner* — Nathan T Leong
(74) *Attorney, Agent, or Firm* — Sunit Talapatra; Foley & Lardner LLP

(57) ABSTRACT

The invention provides a method for preparing tissue-adhesive sheets that may suitably be applied as an implantable haemostatic or sealing construct during surgical procedures, said method comprising:
- providing a fibrous sheet comprising a three-dimensional interconnected interstitial space;
- providing reactive polymer particles comprising a water-soluble electrophilic polymer carrying at least 3 reactive electrophilic groups that are capable of reacting with amine groups in blood under the formation of a covalent bond;
- placing the fibrous sheet and the reactive polymer particles between two electrodes;
- simultaneously subjecting the fibrous sheet and the reactive polymer particles to an electric field of 0.1 to 40 kV/mm to impregnate the interconnected interstitial space of the fibrous sheet with the reactive polymer particles.

15 Claims, No Drawings

(56) References Cited

U.S. PATENT DOCUMENTS

| | | | |
|---|---|---|---|
| 2016/0250013 A1 | 9/2016 | Skalla et al. | |
| 2016/0271228 A1 | 9/2016 | Gulle et al. | |
| 2017/0266337 A1* | 9/2017 | Hoogenboom | A61L 27/18 |
| 2018/0221531 A1 | 8/2018 | Bender et al. | |
| 2019/0231923 A1 | 8/2019 | Hoogenboom et al. | |
| 2019/0374673 A1 | 12/2019 | Hoefinghoff et al. | |
| 2022/0023484 A1 | 1/2022 | Yang et al. | |
| 2022/0133943 A1 | 5/2022 | Keereweer et al. | |

FOREIGN PATENT DOCUMENTS

| | | |
|---|---|---|
| CN | 101978040 A | 2/2011 |
| CN | 102361655 A | 2/2012 |
| CN | 102802683 A | 11/2012 |
| CN | 103429268 A | 12/2013 |
| CN | 104271638 A | 1/2015 |
| CN | 105407931 A | 3/2016 |
| CN | 105727346 A | 7/2016 |
| CN | 106215217 A | 12/2016 |
| CN | 106390177 A | 2/2017 |
| CN | 107106719 A | 8/2017 |
| CN | 108404199 A | 8/2018 |
| CN | 109310803 A | 2/2019 |
| CN | 109646710 A | 4/2019 |
| GB | 2 543 307 A | 4/2017 |
| JP | 2001-521834 A | 11/2001 |
| JP | 2005-253830 A | 9/2005 |
| JP | 2006-523113 A | 10/2006 |
| JP | 2010-520377 A | 6/2010 |
| JP | 4875804 B2 | 2/2012 |
| JP | 2012-509139 A | 4/2012 |
| JP | 2013-523296 A | 6/2013 |
| JP | 2013-526368 A | 6/2013 |
| JP | 2014-503017 A | 2/2014 |
| JP | 2014-533988 A | 12/2014 |
| JP | 2015-511507 A | 4/2015 |
| JP | 2017-008315 A | 1/2017 |
| JP | 2017-531488 A | 10/2017 |
| KR | 20170066450 A | 6/2017 |
| RU | 2593755 C2 | 8/2016 |
| WO | WO-98/12274 A1 | 3/1998 |
| WO | WO-2006/078282 A2 | 7/2006 |
| WO | WO-2010/059280 A2 | 5/2010 |
| WO | WO-2011/124640 A1 | 10/2011 |
| WO | WO-2012/057628 A2 | 5/2012 |
| WO | WO-2013/053759 A2 | 4/2013 |
| WO | WO-2014/190038 A2 | 11/2014 |
| WO | WO-2016/056901 A1 | 4/2016 |
| WO | WO-2021/009014 A1 | 1/2021 |

OTHER PUBLICATIONS

International Search Report and Written Opinion received for PCT Application No. PCT/EP2020/069441, mailed on Oct. 1, 2020, 11 pages.

International Search Report and Written Opinion, received for PCT Application No. PCT/EP2020/069442, mailed on Jul. 31, 2020, 9 pages.

International Search Report and Written Opinion, received for PCT Application No. PCT/EP2020/069443, mailed on Jul. 31, 2020, 10 pages.

Sutagin et al., "Himiâ i fizika polimerov (Chemistry and Physics of Polymers)", Ministry of Education of the Russian Federation Tomsk Polytechnic University, 2 pages, 2003.

* cited by examiner

METHOD FOR PREPARING A TISSUE-ADHESIVE SHEET

CROSS-REFERENCE TO RELATED APPLICATIONS

The present application is a Continuation of International Patent Application No. PCT/EP2020/069445, filed Jul. 9, 2020, which claims priority to European Patent Application No. 19186041.0 filed Jul. 12, 2019; the entire contents of all of which are hereby incorporated by reference.

TECHNICAL FIELD OF THE INVENTION

The present invention relates to a method of preparing a tissue-adhesive sheet, said method comprising:
 providing a fibrous sheet comprising a three-dimensional interconnected interstitial space;
 providing reactive polymer particles comprising a water-soluble electrophilic polymer carrying at least 3 reactive electrophilic groups that are capable of reacting with amine groups in blood under the formation of a covalent bond;
 placing the fibrous sheet and the reactive polymer particles between two electrodes;
 simultaneously subjecting the fibrous sheet and the reactive polymer particles to an electric field of 0.1 to 40 kV/mm to impregnate the interconnected interstitial space of the fibrous sheet with the reactive polymer particles.

The present method enables effective distribution of the reactive polymer particles inside the fibrous sheet and the production of tissue-adhesive sheets with excellent adhesive properties.

BACKGROUND OF THE INVENTION

One of the main challenges during surgical procedures on parenchymatous tissue is to attain control over bleeding. Suture control, electrocautery, and ultrasonic sealing often do not suffice during operations on, for example, liver or kidneys. As a result, procedures like hepatic resections or partial nephrectomy require an alternative approach to control bleeding. For this purpose, a wide range of topical haemostatic products has been developed and are clinically available.

Boerman et al. (*Next Generation Hemostatic Materials Based on NHS-Ester Functionalized Poly(2-oxazoline)s*, Biomacromolecules (2017), 18, 2529-2538) describe a synthetic, nonbioactive hemostatic product that is obtained by coating N-hydroxysuccinimide ester (NHS)-functional poly (2-oxazoline)s (NHS-POx) onto gelatin patches, which acts by formation of covalent cross-links between polymer, host blood proteins, gelatin and tissue to seal the wound site and prevent haemorrhage during surgery.

US 2010/0233246 describes a biocompatible polymer device comprising a collagen sponge or sheet impregnated with a two-part reactive polyethylene glycol powder, wherein said reactive powder comprises a first polyethylene glycol having nucleophilic groups and a second polyethylene glycol having electrophilic groups, wherein the polyethylene glycol powder remains unreactive in the dry state.

US 2011/0250257 describes an anhydrous fibrous sheet comprising a first component of fibrous polymer, said polymer containing electrophilic groups or nucleophilic groups, and a second component capable of crosslinking the first component when said sheet is exposed to an aqueous medium in contact with biological tissue to form a crosslinked hydrogel that is adhesive to the biological tissue; wherein the second component is a fibrous polymer and containing electrophilic groups if the first component contains nucleophilic groups or containing nucleophilic groups if the first component contains electrophilic groups; or the second component is a coating on the fibrous polymer of the first component, wherein said coating contains electrophilic groups if the first component contains nucleophilic groups or nucleophilic groups if the first component contains electrophilic groups; or the second component is a dry powder dispersed and entrapped within interstices of the fibrous polymer of the first component, wherein said powder contains electrophilic groups if the first component contains nucleophilic groups or nucleophilic groups if the first component contains electrophilic groups.

WO 2011/124640 describes a method of manufacturing a hemostatic sponge comprising:
 a) providing a sponge comprising a matrix of a biomaterial in dried form,
 b) providing one reactive polymeric material in the form of dry powder,
 c) contacting a) and b) so that the material of b) is present on at least one surface of said sponge, and
 d) fixing the material of b) on the sponge of a).

Fixation can be achieved by melting for a sufficiently long time period.

WO 2012/057628 describes a tissue-adhesive medical product comprising at least 1% by weight of dry matter of an electrophilically activated polyoxazoline (EL-POx), said EL-POx comprising at least 2 reactive electrophilic groups, including at least one pendant electrophilic group. Besides EL-POx, the medical product may contain a nucleophilically activated polyoxazoline (NU-POx). Examples of tissue-adhesive products include adhesive tissue tape, tissue sealant, haemostatic porous material and implants.

WO 2016/056901 describes an adhesive haemostatic product selected from a coated mesh, a coated foam or a coated powder, said haemostatic product comprising:
 a porous solid substrate having a porosity of at least 5 vol. % and comprising an outer surface that comprises a nucleophilic polymer containing reactive nucleophilic groups;
 an adhesive coating that covers at least a part of the solid substrate, said coating comprising an electrophilically activated polyoxazoline (EL-POx), said EL-POx containing on average at least 1 reactive electrophilic group.

The adhesive haemostatic product is produced by a process comprising the steps of providing a porous solid substrate; coating the substrate with a coating liquid that comprises EL-POx and a solvent; and removing the solvent.

U.S. Pat. No. 6,733,845 describes process for the electrostatic impregnation into a fibrous or filamentary network with powder, for producing a composite comprising a rigid or flexible matrix with which said network is in intimate contact, wherein the powder and said network of fibers or filaments are placed between two electrodes, said electrodes being electrically isolated insulated from each other and said electrodes being connected respectively to the oppositely charged poles of an AC voltage electrostatic generator so as to simultaneously subject said powder and said fibrous or filamentary network lying between said electrodes to an electrostatic field, the AC voltage of which is at least 5 kV, for a time of at least 2 seconds.

SUMMARY OF THE INVENTION

The inventors have developed a method for preparing tissue-adhesive sheets that may suitably be applied as an implantable haemostatic or sealing construct during surgical procedures. The present method comprises:
- providing a fibrous sheet comprising a three-dimensional interconnected interstitial space;
- providing reactive polymer particles comprising a water-soluble electrophilic polymer carrying at least 3 reactive electrophilic groups that are capable of reacting with amine groups in blood under the formation of a covalent bond;
- placing the fibrous sheet and the reactive polymer particles between two electrodes;
- simultaneously subjecting the fibrous sheet and the reactive polymer particles to an electric field of 0.1 to 40 kV/mm to impregnate the interconnected interstitial space of the fibrous sheet with the reactive polymer particles.

When blood is absorbed by the tissue-adhesive sheet of the present invention as it enters the interstitial space, the reactive polymer particles within the sheet start dissolving as soon as they are 'wetted' by the blood, thereby allowing the electrophilic polymer to react with both reactive nucleophilic groups in the blood and tissue, resulting in blood coagulation and tissue sealing, both of which contribute to haemostasis. The haemostatic properties of fibrous sheets containing reactive polymer particles benefit from a 'deep' impregnation with, and a homogeneous distribution of the reactive polymer particles within the fibrous sheet. The present method makes it possible to achieve both desirables.

In addition, the present method offers the advantage that, unlike impregnation with liquids, it does not affect the structural integrity or mechanical properties of the fibrous sheet. Furthermore, in comparison to mechanical impregnation methods that make use of shaking or vibration, the present method does not impose mechanical stress and achieves a more effective impregnation, especially with very small (<100 µm) reactive polymer particles.

Another aspect of the present invention relates to a tissue-adhesive sheet that is obtained by the present method.

DETAILED DESCRIPTION OF THE INVENTION

A first aspect of the invention relates to a method of preparing a tissue-adhesive sheet, said method comprising:
- providing a fibrous sheet comprising a three-dimensional interconnected interstitial space;
- providing reactive polymer particles comprising a water-soluble electrophilic polymer carrying at least 3 reactive electrophilic groups that are capable of reacting with amine groups in blood under the formation of a covalent bond;
- placing the fibrous sheet and the reactive polymer particles between two electrodes;
- simultaneously subjecting the fibrous sheet and the reactive polymer particles to an electric field of 0.1 to 40 kV/mm to impregnate the interconnected interstitial space of the fibrous sheet with the reactive polymer particles.

The term "tissue-adhesive" as used herein refers to the ability of the tissue-adhesive sheet to cling to tissue due to the formation of covalent bonds between the sheet and the tissue. Formation of these covalent bonds typically requires the presence of water. The term "interstitial space" as used herein refers to the void ("empty") space within the fibrous sheet. The interstitial space within the fibrous sheet allows the introduction of reactive polymer particles into the sheet. Also blood and other bodily fluids can enter the interstitial space, allowing the water-soluble electrophilic polymer within the reactive polymer particles to dissolve.

The "water-soluble electrophilic polymer carrying reactive electrophilic groups" that is employed in accordance with the present invention carries at least three reactive groups that are capable of reacting with amine groups in tissue and blood under the formation of a covalent bond. This water-soluble electrophilic polymer has a molecular weight of at least 1 kDa and a solubility in distilled water of 20° C. of at least 50 g/L.

The term "water absorption capacity" as used herein is a measure of the capability of the tissue-adhesive sheet to absorb water. The water absorption capacity is determined by weighing a sample of the dry sheet (weight=$W_d$) followed by immersion of the sample into distilled water (37° C.) for 45 minutes. Next, the sample is removed from the water and water clinging to the outside of the substrate is removed, following which the sample is weighed again (weight=$W_w$). The water absorption capacity=$100\% \times (W_w - W_d)/W_d$. The water adsorption capacity is indicative of the porosity of the substrate as well as of its ability to swell in the presence of water.

The term "collagen" as used herein refers the main structural protein in the extracellular space of various connective tissues in animal bodies. Collagen forms a characteristic triple helix of three polypeptide chains. Depending upon the degree of mineralization, collagen tissues may be either rigid (bone) or compliant (tendon) or have a gradient from rigid to compliant (cartilage). Unless indicated otherwise, the term "collagen" also encompasses modified collagens other than gelatin.

The term "gelatin" as used herein refers to a mixture of peptides and proteins produced by partial hydrolysis of collagen extracted from the skin, bones, and connective tissues of animals such as domesticated cattle, chicken, pigs, and fish. During hydrolysis, the natural molecular bonds between individual collagen strands are broken down into a form that rearranges more easily.

The term "polyoxazoline" as used herein refers to a poly(N-acylalkylenimine) or a poly(aroylalkylenimine) and is further referred to as POx. An example of POx is poly(2-ethyl-2-oxazoline). The term "polyoxazoline" also encompasses POx copolymers.

The reactive polymer particles may be homogeneously distributed within the interstitial space of the fibrous sheet in the sense that the particle density is essentially the same throughout the sheet. The reactive polymer particles may be unevenly distributed through the thickness of the sheet. For certain applications it may be advantageous if the reactive polymer particle density shows a gradient, e.g. in that the density of reactive polymer particles is lowest near the side of the sheet that is meant to applied onto a bleeding wound and highest near the other side of the sheet.

The diameter distribution of the reactive polymer particles may suitably be determined by means of laser diffraction using a Malvern Mastersizer 2000 in combination with the Stainless Steel Sample Dispersion Unit. The sample dispersion unit is filled with approx. 120 ml of cyclohexane, which is stabilized for 5 to 10 minutes at a stirring speed of 1800 rpm, followed by a background measurement (blanc measurement). The sample tube is shaken and turned horizontally for 20 times. Next, about 50 mg is dispersed in the sample dispersion unit containing the cyclohexane. After the sample is introduced in the dispersion unit, the sample is stirred for one and a half minute at 1800 rpm to ensure that all particles are properly dispersed, before carrying out the measurement. No ultrasonic treatment is performed on the dispersed particles. Mean particle size is expressed as D [4,3], the volume weighted mean diameter (ΣniDi$^4$)/(ΣniDi$^3$).

In a preferred embodiment, the present method comprises impregnating the fibrous sheet with 5-90%, more preferably 10-80%, even more preferably 20-75% and most preferably 50-70% of the reactive polymer particles, said percentage being calculated by weight of the fibrous sheet.

According to a particularly preferred embodiment, the tissue-adhesive sheet of the present invention is bio-absorbable, meaning that the sheet, the reactive polymer particles and any other components of the tissue-adhesive sheet are eventually absorbed in the body. Absorption of the sheet and reactive polymer particles typically requires chemical decomposition (e.g. hydrolysis) of polymers contained therein. Complete bio-absorption of the tissue-adhesive sheet by the human body is typically achieved in 1 to 10 weeks, preferably in 2 to 8 weeks.

The tissue-adhesive sheet of the present invention is preferably sterile.

The tissue-adhesive sheet of the present invention typically has a non-compressed mean thickness of 0.5-25 mm. More preferably, the non-compressed mean thickness is in the range of 1-10 mm, most preferably in the range of 1.5-5 mm.

The tissue-adhesive sheet preferably has a non-compressed density of less than 200 mg/cm$^3$, more preferably of less than 150 mg/cm$^3$ and most preferably of 10-100 mg/cm$^3$.

The tissue-adhesive sheet of the present invention preferably is essentially anhydrous.

Typically, the tissue-adhesive sheet has a water content of not more than 5 wt. %, more preferably of not more than 2 wt. % and most preferably of not more than 1 wt. %.

The water absorption capacity of the tissue-adhesive sheet preferably is at least 50%, more preferably lies in the range of 100% to 800%, most preferably in the range of 200% to 500%.

The fibrous sheet employed in the present method preferably is water-resistant, i.e. the sheet is not water soluble and does not disintegrate in water at neutral pH conditions (pH 7) and a temperature of 37° C.

The fibres in the fibrous sheet preferably have a mean diameter of 1-500 µm, more preferably of 2-300 µm and most preferably of 5-200 µm. The mean diameter of the fibres can suitably be determined using a microscope.

Typically, at least 50 wt. %, more preferably at least 80 wt. % of the fibres in the fibrous sheet have a diameter of 1-300 µm and a length of at least 1 mm.

Preferably, at least 50 wt. %, more preferably at least 80 wt. % of the fibres in the fibrous sheet have an aspect ratio (ratio of length to diameter) of at least 1000.

The fibrous sheet preferably comprises at least 50 wt. %, more preferably at least 80 wt. % and most preferably at least 90 wt. % fibres containing gelatin, collagen, cellulose, modified cellulose, carboxymethyldextran, PLGA, sodium hyaluronate/carboxy methylcellulose, polyvinyl alcohol, chitosan or a combination thereof.

In an embodiment of the invention, the fibrous carrier structure does not comprise oxidised regenerated cellulose.

Preferred fibrous sheets have an open pore structure with a permeability to air of at least 0.1 L/min×cm$^2$, more preferably of at least 0.5 L/min×cm$^2$. The air permeability is determined in accordance with EN ISO 9237:1995 (Textiles—Determination of the permeability of fabrics to air).

The fibres in the fibrous sheet can be produced by means of methods known in the art, such as electrospinning, electro-blown spinning and high speed rotary sprayer spinning. Production of fibrous sheet by means of high speed rotary sprayer spinning is described in US 2015/0010612. It is also possible to use commercially available haemostatic fibrous sheets as the fibrous sheet.

The reactive polymer particles employed in the present method preferably contain at least 10 wt. % of the water-soluble electrophilic polymer. More preferably, the reactive polymer particles contain at least 50 wt. %, more preferably at least 90 wt. % of the water-soluble electrophilic polymer.

The present method offers the advantage that, unlike impregnation techniques that make use shaking or vibration, it can effectively distribute very small particles of reactive polymer into the fibrous sheet. This is advantageous as small particles due to the high surface/volume ratio, dissolve faster than larger particles. Thus, the haemostatic properties of tissue-adhesive sheets containing very small reactive polymer particles are generally superior to tissue-adhesive sheets containing larger reactive polymer particles. Accordingly, in a very preferred embodiment, the reactive polymer particles have a volume weighted mean diameter (D [4,3], (Σn$_i$D$^4$)/(Σn$_i$D$^3$)) in the range of 10-100 µm, more preferably in the range of 15-80 µm and most preferably in the range of 20-70 µm.

According to a particularly preferred embodiment at least 80 vol. % of the reactive polymer particles has a diameter in the range of 5-200 µm, more preferably in the range of 10-120 µm and most preferably in the range of 12-100 µm.

The reactive polymer particles of the present invention may be prepared in various ways, e.g. by milling, by spray drying a polymeric solution, by freeze drying, by spray chilling a polymeric melt, by granulating a powder mixture, or by fluidised bed coating.

The water-soluble electrophilic polymer that is contained in the reactive polymer particles typically has a molecular weight of at least 2 kDa, more preferably of at least 5 kDa and most preferably of 10-100 kDa.

The water-soluble electrophilic polymer preferably has a solubility in distilled water of 20° C. of at least 100 g/L, more preferably of at least 200 g/L.

The water-soluble electrophilic polymer that is employed in accordance with the present invention, preferably contains at least 4 reactive electrophilic groups, more preferably at least 8 reactive electrophilic groups, even more preferably at least 16 reactive electrophilic groups and most preferably at least 32 reactive electrophilic groups.

The water-soluble electrophilic polymer that is present in the reactive polymer particles is preferably selected from polyoxazolines, polyethylene glycols, polyvinylpyrrolidones, polyurethanes (e.g. as described in WO 2017/171551) and combinations thereof. Even more preferably the electrophilic polymer is selected from polyoxazolines, polyethylene glycols and combinations thereof. Most preferably the electrophilic polymer is a polyoxazoline.

The polyoxazoline comprising reactive electrophilic groups is preferably derived from a polyoxazoline whose repeating units are represented by the following formula (I):

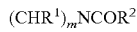

wherein R$^2$, and each of R$^1$ are independently selected from H, optionally substituted C$_{1-22}$ alkyl, optionally substituted cycloalkyl, optionally substituted aralkyl, optionally substituted aryl; and m being 2 or 3.

Preferably, R$^1$ and R$^2$ in formula (I) are selected from H and C$_{1-8}$ alkyl, even more preferably from H and C$_{1-4}$ alkyl. R$^1$ most preferably is H. The integer m in formula (I) is preferably equal to 2.

According to a preferred embodiment, the polyoxazoline is a polymer, even more preferably a homopolymer of 2-alkyl-2-oxazoline, said 2-alkyl-2-oxazoline being selected from 2-methyl-2-oxazoline, 2-ethyl-2-oxazoline, 2-propyl-2-oxazoline, 2-butyl-2-oxazoline and combinations thereof. Preferably, the polyoxazoline is a homopolymer of 2-propyl-2-oxazoline or 2-ethyl-oxazoline. Most preferably, the polyoxazoline is a homopolymer of 2-ethyl-oxazoline.

According to a particularly preferred embodiment, the water-soluble electrophilic polymer comprises at least 20 oxazoline units, more preferably at least 30 oxazoline units and most preferably at least 80 oxazoline units. The electrophilic polymer preferably comprises on average at least 0.05 reactive electrophilic groups per oxazoline residue. Even more preferably, the electrophilic polymer comprises on average at least 0.1 reactive electrophilic groups per oxazoline residue. Most preferably, the electrophilic polymer comprises on average 0.12-0.5 reactive electrophilic groups per oxazoline residue.

The water-soluble electrophilic polymer typically carries on average at least 10, more preferably at least 20 reactive electrophilic groups.

Polyoxazoline can carry reactive electrophilic groups in its side chains (pendant reactive electrophilic groups), at its termini, or both. The polyoxazoline that is employed in accordance with the present invention advantageously contains one or more pendant reactive electrophilic groups. Typically, the polyoxazoline contains 0.03-0.5 pendant reactive electrophilic groups per monomer, more preferably 0.04-0.35 pendant reactive electrophilic groups per monomer, even more preferably 0.05-0.25 pendant reactive electrophilic groups per monomer.

The polyethylene glycol (PEG) comprising reactive electrophilic groups that is applied in accordance with the present invention preferably is a multi-arm PEG or a star PEG, comprising at least 3 arms, more preferably at least 4 arms terminated with a reactive electrophilic group.

The reactive polymer particles in the tissue-adhesive sheet preferably comprise a water-soluble electrophilic polymer that carries reactive electrophilic groups selected from carboxylic acid esters, sulfonate esters, phosphonate esters, pentafluorophenyl esters, p-nitrophenyl esters, p-nitrothiophenyl esters, acid halide groups, anhydrides, ketones, aldehydes, isocyanato, thioisocyanato, isocyano, epoxides, activated hydroxyl groups, olefins, glycidyl ethers, carboxyl, succinimidyl esters, sulfo succinimidyl esters, maleimido (maleimidyl), ethenesulfonyl, imido esters, aceto acetate, halo acetal, orthopyridyl disulfide, dihydroxy-phenyl derivatives, vinyl, acrylate, acrylamide, iodoacetamide and combinations thereof. More preferably, the reactive electrophilic groups are selected from carboxylic acid esters, sulfonate esters, phosphonate esters, pentafluorophenyl esters, p-nitrophenyl esters, p-nitrothiophenyl esters, acid halide groups, anhyinidrides, ketones, aldehydes, isocyanato, thioisocyanato, isocyano, epoxides, activated hydroxyl groups, glycidyl ethers, carboxyl, succinimidyl esters, sulfo succinimidyl esters, imido esters, dihydroxy-phenyl derivatives, and combinations thereof. Even more preferably, the reactive electrophilic groups are selected from halo acetals, orthopyridyl disulfide, maleimides, vinyl sulfone, dihydroxyphenyl derivatives, vinyl, acrylate, acrylamide, iodoacetamide, succinimidyl esters and combinations thereof. Most preferably, the reactive electrophilic groups are selected from maleimides, vinyl, acrylate, acrylamide, succinimidyl esters, sulfo succinimidyl esters and combinations thereof.

Examples of succinimidyl esters that may be employed include succinimidyl glutarate, succinimidyl propionate, succinimidyl succinamide, succinimidyl carbonate, disuccinimidyl suberate, bis(sulfosuccinimidyl) suberate, dithiobis(succinimidylpropionate), bis(2-succinimidooxycarbonyloxy) ethyl sulfone, 3,3'-dithiobis(sulfosuccinimidylpropionate), succinimidyl carbamate, sulfosuccinimidyl(4-iodoacetyl)aminobenzoate, bis(sulfosuccinimidyl) suberate, sulfosuccinimidyl-4-(N-maleimidomethyl)-cyclohexane-1-carboxylate, dithiobis-sulfosuccinimidyl propionate, disulfo-succinimidyl tartarate; bis[2-(sulfo-succinimidyloxycarbonyloxyethylsulfone)], ethylene glycol bis (sulfosuccinimiclylsuccinate), dithiobis-(succinimidyl propionate).

Examples of dihydroxyphenyl derivatives that may be employed include dihydroxyphenylalanine, 3,4-dihydroxyphenylalanine (DOPA), dopamine, 3,4-dihydroxyhydroccinamic acid (DOHA), norepinephrine, epinephrine and catechol.

In an advantageous embodiment of the present invention, besides the water-soluble electrophilic polymer, the reactive polymer particles additionally contain a nucleophilic cross-linking agent that contains at least two reactive nucleophilic groups that are capable of reacting with the reactive electrophilic groups of the water-soluble electrophilic polymer under the formation of a covalent bond. The introduction of a nucleophilic cross-linking agent offers the advantage that the haemostatic and adhesive properties of the sheet can be improved as the water-soluble electrophilic polymer will react with the nucleophilic cross-linking agent when blood enters the sheet. This cross-linking reaction will lead to the formation of a hydrogel that immobilizes the blood flow and this hydrogel will stick to tissue due to the formation of covalent bonds between reactive electrophilic groups in the hydrogel and amine/thiol groups in the tissue. By combining the water-soluble electrophilic polymer and the nucleophilic cross-linking agent in a single particle, it is ensured that these two reactive components can be homogeneously distributed throughout the haemostatic sheet, that no segregation occurs during transport and handling, and that these components can react immediately with each other when the particles come into contact with blood.

Reactive polymer particles containing a combination of the water-soluble polymer carrying reactive electrophilic groups and a nucleophilic cross-linking agent, i.e. reactive hybrid particles, can be produced via wet granulation and subsequent drying, preferably under reduced pressure. The granulation liquid should be chosen such that little or no reactions occur during granulation between the water-soluble electrophilic polymer and the nucleophilic cross-linking agent. This may be achieved, for instance, by employing a granulation liquid in which at least one of these two components is insoluble. Most preferably, the water-soluble polymer carrying reactive electrophilic groups is insoluble in the granulation liquid.

According to a particularly preferred embodiment, the reactive polymer particles are particle agglomerates comprising: (i) electrophilic particles containing the water-soluble electrophilic polymer; and (ii) nucleophilic particles containing the nucleophilic cross-linking agent.

The electrophilic particles preferably contain at least 30 wt. %, more preferably at least 50 wt. % and most preferably at least 80 wt. % of the water-soluble electrophilic polymer.

The nucleophilic particles preferably contain at least 30 wt. %, more preferably at least 50 wt. % and most preferably at least 80 wt. % of the nucleophilic cross-linking agent.

The nucleophilic cross-linking agent preferably contains at least 3 reactive nucleophilic groups. The reactive nucleophilic groups of the nucleophilic cross-linking agent are preferably selected from amine groups, thiol groups and combinations thereof. More preferably, these reactive nucleophilic groups are amine groups. According to a preferred embodiment, the reactive nucleophilic groups present in the nucleophilic cross-linking agent are primary amine groups.

Preferably, the nucleophilic cross-linking agent is selected from protein, chitosan, synthetic polymers carrying reactive nucleophilic group, carbohydrate polymers carrying reactive nucleophilic groups and combinations thereof. Even more preferably, the nucleophilic cross-linking agent is selected from gelatin, collagen, chitosan and combinations thereof.

In the present method the fibrous sheet and the reactive polymer particles are preferably simultaneously subjected to an electric field of 0.5 to 30 kV/mm, more preferably to an electric field of 1 to 10 kV/mm.

According to a particularly preferred embodiment, the fibrous sheet and the reactive polymer particles are simultaneously subjected to an alternating electric field. Preferably, the electric field is alternated with a frequency of at least 10 $s^{-1}$, more preferably with a frequency of at least 50 $s^{-1}$ and most preferably with a frequency of 100 $s^{-1}$.

Impregnation of the fibrous sheet may effectively be achieved in the present method by creating a layer of the reactive polymer particles adjacent to the fibrous sheet and by placing the fibrous sheet and the adjacent layer of reactive polymer particles between the two electrodes. Impregnation may also be achieved by creating a laminate containing two or more fibrous sheets separated by layers of reactive polymer particles and by placing this laminate between the two electrodes.

In a preferred embodiment of the present method, the fibrous sheet and the reactive polymer particles are placed between a lower electrode and an upper electrode, these electrodes being electrically insulated from each other by a dielectric and connected to the respective poles of an AC generator so as to simultaneously subject the fibrous sheet and the reactive polymer particles to the electric field.

The fibrous sheet and the reactive polymer particles are preferably passed between the lower electrode and upper electrode whilst simultaneously subjecting the fibrous sheet and the reactive polymer particles to the electric field. Thus, a roll of fibrous sheet may suitably be impregnated with the reactive polymer particles by the present method in a semi-continuous fashion.

In a preferred embodiment, the fibrous sheet and the reactive polymer particles are simultaneously exposed to the electric field for at least 0.1 second, more preferably for at least 5 seconds and most preferably for at least 30 seconds.

Another aspect of the invention relates to a tissue-adhesive sheet obtained by the method as described herein before.

The invention is further illustrated by the following non-limiting examples.

EXAMPLES

In general: wherever residual moisture content (in dried powder, granulate and/or fibrous sheets) after drying is not explicitly mentioned, levels are below 2.0% w/w.

Powders having a D [4,3] of 40 µm or less, were produced by milling, followed by sieving over a 250 mesh sieve (Haver and Boecker, serial number 47181315). Particles that did not pass through the sieve were milled again and sieved again until all powder was below 250 mesh.

Preparation of Water-Soluble Electrophilic Polymer (NHS-POx)

NHS-side chain activated poly[2-(ethyl/hydroxy-ethyl-amide-ethyl/NHS-ester-ethyl-ester-ethyl-amide-ethyl)-2-oxazoline] terpolymer containing 20% NHS-ester groups (=EL-POx, 20% NHS) was synthesized as follows:

Poly[2-(ethyl/methoxy-carbonyl-ethyl)-2-oxazoline] copolymer (DP=+/−100) was synthesized by means of CROP using 60% 2-ethyl-2-oxazoline (EtOx) and 40% 2-methoxycarbonyl-ethyl-2-oxazoline (MestOx). A statistical copolymer containing 40% 2-methoxycarbonyl-ethyl groups ($^1$H-NMR) was obtained. Secondly, the polymer containing 40% 2-methoxycarbonyl-ethyl groups, was reacted with ethanolamine yielding a copolymer with 40% 2-hydroxy-ethyl-amide-ethyl-groups ($^1$H-NMR). After that, half of the 2-hydroxy-ethyl-amide-ethyl-groups was reacted with succinic anhydride yielding a terpolymer with 60% 2-ethyl groups, 20% 2-hydroxy-ethyl-amide-ethyl-groups and 20% 2-carboxy-ethyl-ester-ethyl-amide-ethyl-groups according to $^1$H-NMR. Lastly, the 2-carboxy-ethyl-ester-ethyl-amide-ethyl-groups were activated by N-hydroxysuccinimide (NHS) and diisopropylcarbodiimide (DIC), yielding EL-POx, 20% NHS. The NHS-POx contained 20% NHS-ester groups according to $^1$H-NMR. NHS-POx was dissolved between 2-8° C. in water (60 g in 300 mL), cooled at minus 80° C. for half an hour and freeze dried. The freeze dried powder so obtained was dried in a Rotavap at 40° C. until the water content was below 0.8% w/w as determined via Karl Fischer titration. This dry (white) powder was grinded using either a Retsch Ultra Centrifugal Mill ZM 200 with a 12 teeth push-fit rotor combined with a distance sieve having trapezoid holes of 0.25 mm until the average particle size was not more than 35 µm (D [4,3]) or a table top coffee grinder until the average particle size was about 70 µm (D [4,3]) and vacuum sealed in alu-alu bags.

Dying of NHS-POx Powder 20 g of NHS-POx powder were dissolved in water and mixed with 50 mg Brilliant Blue FCF (Sigma Aldrich) using a high-performance dispersing instrument (Ultra-Turrax, IKA). Directly after mixing (2 minutes) the solution was frozen at −78° C. and subsequently freeze dried overnight. The freeze dried powder so obtained was dried in a Rotavap at 40° C. until the residual water content was below 0.8% w/w as determined via Karl Fischer titration. Next, the dried (blue) powder was grinded using a Retsch Ultra Centrifugal Mill ZM 200 until a blue dyed NHS-POx powder having an average particle size of not more than 35 µm (D [4,3]) and vacuum sealed in alu-alu bags.

Preparation of Nucleophilic Cross-Linker (NU-POx)

Polyoxazoline containing ethyl and amine groups in the alkyl side chain was synthesized by CROP of EtOx and MestOx and subsequent amidation of the methyl ester side chains with ethylene diamine to yield a poly(2-ethyl/aminoethylamidoethyl-2-oxazoline) copolymer (NU-POx). The NU-POx contained 10% $NH_2$ according to $^1$H-NMR. NU-POx was dissolved between 2-8° C. in water (60 g in 300 mL), cooled at minus 80° C. for half an hour an freeze dried. The freeze dried powder so obtained was dried in a Rotavap at 40° C. until the water content was below 0.8% w/w as determined via Karl Fischer titration. This dry powder was grinded using a Retsch Ultra Centrifugal Mill ZM 200 until the average particle size was not more than 35 µm (D [4,3]) and vacuum sealed in alu-alu bags.

Preparation of Reactive Polymer Particles (NHS-POx/NU-POx Granules)

Blue or white (non-dyed) NHS-POx powder was wetted with isopropyl alcohol (IPA) in a high shear mixer until a homogeneous snow-like powder was obtained containing about 1-2% w/w IPA. After this, NU-POx powder was added and mixed. The wetted blue NHS-POx powder was mixed with NU-POx powder in a molar ratio of 1:1, said molar ratio referring to the ratio of the number of NHS groups provided by NHS-POx to the number of amine groups provided by the NU-POx.

After mixing, the wet granulates were dried under reduced pressure until the IPA content was less than 0.1% w/w as determined via $^1$H-NMR. The dried granulates were grinded using a Retsch Ultra Centrifugal Mill ZM 200 until the average particle size was not more than 50 μm or 35 μm (D [4,3]) and vacuum sealed in alu-alu bags.

The NHS-PDX/NU-POx granulate (1:1) was analysed using $^1$H-NMR spectroscopy. 25 mg of granulate were dissolved in trifluoroacetic acid (0.20 mL) by sonicating for 20 minutes. After complete dissolution of the granulate, the sample was diluted with deuterated dimethylsulfoxide (DMSO-$d_6$) containing maleic acid (2.5 mg/mL) as an internal standard (0.80 mL), transferred to an NMR tube and a $^1$H-NMR spectrum was recorded. From the acquired spectrum, the amount of NHS bound to NHS-POx can be calculated, along with the molar ratio of NHS and amine groups present in the granulate. The amount of NHS bound to NHS-POx in the granulate was equal to the amount of NHS bound to NHS-POx starting material indicating no decay or cross linking during granulation.

The total polymer recovery, i.e. the combination of NHS-POx and NU-POx, in the NMR sample was determined using a known amount of internal standard (maleic acid) and a calibration curve constructed from $^1$H-NMR spectra recorded of NHS-POx and NU-POx in different concentrations. The total polymer recovery was measured to be 99 percent, indicating that no insoluble crosslinked material was formed.

The NHS-PDX/NU-POx granulate (1:1) was further analysed by means of size exclusion chromatography. 20 mg of the granulate was treated with acetic anhydride (1.00 mL) for 1 hour at 50° C. Subsequently, methanol (2.00 mL) was added and the mixture was stirred for an additional hour at 50° C. An aliquot (0.75 mL) was taken and all volatiles were removed under reduced pressure. The sample was taken up in N,N-dimethylacetamide containing 50 mM lithium chloride (2.50 mL), which was the eluent for SEC analysis. SEC was measured against poly(methyl methacrylate) standards and from the obtained size exclusion chromatogram, the $M_n$, $M_w$ and PDI were determined. The PDI was not more than 1.5, indicating no cross linking had occurred during granulation. Analytical validation of this size exclusion chromatographic method indicated that intentional cross linking of NHS-POx with NU-POx at a level of 0.05 mol % increased the PDI to more than 2.5.

Preparation of Reactive Polymer Particles (NHS-POx/NU-POx/P188 Granules)

Reactive NHS-POx/NU-POx granules were prepared as described previously. Subsequently, 1.5%, 2.5%, 3.5%, 5% and 10% w/w P188 coated reactive NHS-POx/NU-POx granulate was prepared by heating the NHS-POx/NU-POx granulate together with P188 powder in a high shear mixer at 65° C. for 10 minutes followed by cooling down to ambient conditions. The coated granulate was grinded using a Retsch Ultra Centrifugal Mill ZM 200 until the average particle size was not more than 40 μm (D [4,3]) and vacuum sealed in alu-alu bags.

The particle size distribution of the granulates so obtained was approximately: 90 vol. %<80 μm, 50 vol. %<40 μm and 10 vol. %<10 μm.

The NHS-POx/NU-POx/P188 granulates were analysed using $^1$H-NMR spectroscopy. 25 mg of powder were dissolved in trifluoroacetic acid (0.20 mL) by sonicating for 20 minutes. After complete dissolution of the granulate, the sample was diluted with deuterated dimethylsulfoxide (DMSO-$d_6$) (0.80 mL), transferred to an NMR tube and a $^1$H-NMR spectrum was recorded. From the obtained spectrum, the amount of non-reacted NHS was calculated to be 98 percent compared to NHS-POx.

The NHS-POx/NU-POx/P188 granulate was further analysed by means of size exclusion chromatography. 20 mg of the granulate was treated with acetic anhydride (1.00 mL) for 1 hour at 50° C. Subsequently, methanol (2.00 mL) was added and the mixture was stirred for an additional hour at 50° C. An aliquot (0.75 mL) was taken and all volatiles were removed under reduced pressure. The sample was taken up in N,N-dimethylacetamide containing 50 mM lithium chloride (2.50 mL), which was the eluent for SEC analysis. SEC was measured against poly(methyl methacrylate) standards and from the obtained size exclusion chromatogram, the $M_n$, $M_w$ and PDI were determined. The PDI was not more than 1.5, indicating that no cross linking had occurred during granulation.

Preparation of Reactive Polymer Particles (NHS-POx/Gelita Spon Granules)

7.01 g of pre-dried gelatin powder (Gelita-SPON®, ex Gelita Medical GmbH), having a water content of less than 0.2% w/w, was dispersed in dichloromethane (200 mL) using a high shear mixer operating at 20,000 rpm for 20 minutes. Subsequently, NHS-POx (7.02 g) was added and the stirring was continued for 5 minutes. NHS-POx did not dissolve. All volatiles were removed from the suspension under reduced pressure. The obtained powder was milled using a coffee grinder until the average particle size was not more than 95 μm (D [4,3]) and vacuum sealed in alu-alu bags, further dried under reduced pressure and vacuum sealed in an alu-alu bag.

The particle size distribution of the granulates so obtained was approximately: 90 vol. %<190 μm, 50 vol. %<80 μm and 10 vol. %<15 μm.

The granulate was analysed by means of $^1$H-NMR spectroscopy analysis. To this end deuterated chloroform (CDCl$_3$) containing 5% (v/v) acetic acid (1.0 mL) was added to 25 mg of the granulate. NHS-POx was selectively extracted by sonicating the sample for 20 minutes. The dispersion was passed through a 0.22 μm filter, transferred to an NMR tube and a $^1$H-NMR spectrum was recorded. From the obtained spectrum, the amount of non-reacted NHS was calculated to be 97 percent compared to NHS-POx.

The granulate was further analysed by means of size exclusion chromatography (SEC) analysis. An aliquot (0.15 mL) of the filtered NHS-POx extract described above was diluted with N,N-dimethylacetamide containing 50 mM lithium chloride (1.00 mL), which was the eluent for SEC analysis. The sample was analysed by SEC against poly (methyl methacrylate) standards and the PDI was 1.45 indicating that no cross linking had occurred.

Preparation of Reactive Polymer Particles (NHS-POx/NU-POx/PEG 3000 Granules)

Reactive NHS-POx/NU-POx granules were prepared as described previously. Subsequently, 5% and 10% w/w PEG 3000 coated reactive NHS-POx/NU-POx granulate was prepared by heating the NHS-POx/NU-POx granulate together with PEG (MW 3 kDa) powder in a high shear mixer at 65° C. for 10 minutes followed by cooling down to ambient conditions. The coated granulate was grinded using a Retsch Ultra Centrifugal Mill ZM 200 and vacuum sealed in alu-alu bags.

The NHS-POx/NU-POx/PEG 3000 granulates were analysed using $^1$H-NMR spectroscopy. 25 mg of powder were dissolved in trifluoroacetic acid (0.20 mL) by sonicating for 20 minutes. After complete dissolution of the granulate, the sample was diluted with deuterated dimethylsulfoxide (DMSO-$d_6$) (0.80 mL), transferred to an NMR tube and a $^1$H-NMR spectrum was recorded. From the obtained spectrum, the amount of non-reacted NHS was calculated to be 96 percent compared to NHS-POx.

The NHS-POx/NU-POx/PEG granulate was further analysed by means of size exclusion chromatography. 20 mg of the granulate was treated with acetic anhydride (1.00 mL) for 1 hour at 50° C. Subsequently, methanol (2.00 mL) was added and the mixture was stirred for an additional hour at 50° C. An aliquot (0.75 mL) was taken and all volatiles were removed under reduced pressure. The sample was taken up in N,N-dimethylacetamide containing 50 mM lithium chloride (2.50 mL), which was the eluent for SEC analysis. SEC was measured against poly(methyl methacrylate) standards and from the obtained size exclusion chromatogram, the $M_n$, $M_w$ and PDI were determined. The PDI was not more than 1.5, indicating that no cross linking had occurred during granulation.

Preparation of Reactive Polymer Particles (NHS-POx/NU-PEG)

5% w/w NU-PEG coated NHS-POx was prepared by heating NHS-POx (D [4,3]≤35 μm) together with PEG diamine (MW 10 kDa) powder in a high shear mixer at 65° C. for 10 minutes followed by cooling down to ambient conditions. The coated granulate was grinded using a Retsch Ultra Centrifugal Mill ZM 200 and vacuum sealed in alu-alu bags.

The NHS-POx/NU-PEG reactive polymer particles were analysed using $^1$H-NMR spectroscopy. 25 mg of powder were dissolved in trifluoroacetic acid (0.20 mL) by sonicating for 20 minutes. After complete dissolution of the granulate, the sample was diluted with deuterated dimethylsulfoxide (DMSO-$d_6$) (0.80 mL), transferred to an NMR tube and a $^1$H-NMR spectrum was recorded. From the obtained spectrum, the amount of non-reacted NHS was calculated to be 95 percent compared to NHS-POx.

The NHS-POx/NU-PEG reactive polymer particles were further analysed by means of size exclusion chromatography. 20 mg of powder was treated with acetic anhydride (1.00 mL) for 1 hour at 50° C. Subsequently, methanol (2.00 mL) was added and the mixture was stirred for an additional hour at 50° C. An aliquot (0.75 mL) was taken and all volatiles were removed under reduced pressure. The sample was taken up in N,N-dimethylacetamide containing 50 mM lithium chloride (2.50 mL), which was the eluent for SEC analysis. SEC was measured against poly(methyl methacrylate) standards and from the obtained size exclusion chromatogram, the $M_n$, $M_w$ and PDI were determined. The PDI was not more than 1.5, indicating that no cross linking had occurred during granulation.

Fibrous Sheets

The following commercially available haemostatic products were selected to be used as fibrous sheets in the preparation of tissue-adhesive sheets according to the present invention:

Gelita Tuft-It®: A cohesive fibrous sheet consisting of eight layers of reduced cross-linked gelfoam fibres. The eight layers, of each about 2 mm thickness, have dimensions of 50 mm by 75 mm. The water content of Gelita Tuft-It® is not more than 15%. The product was dried in a vacuum oven for several hours at 40° C. to reduce the water content to not more than 2.0% w/w (determined gravimetrically), before it was impregnated with agglomerate particles.

SURGICEL® SNoW™: a cohesive fibrous sheet consisting of absorbable non-woven fabric prepared by the controlled oxidation of regenerated cellulose (ORC). Dimensions are 5.1 cm×10.2 cm and the water content was not more than 2.0% w/w SURGICEL® NU-KNIT®/SURGICEL® SNoW™-Hybrid: a densely knit absorbable fabric of fibres prepared by the controlled oxidation of regenerated cellulose (ORC), available in several sizes (e.g., 15.2 cm×22.9 cm) stitched onto SURGICEL® SNoW™ cut to a dimension of 5.1 cm×10.2 cm.

PEM: a cohesive fibrous sheet consisting of oxidized regenerated cellulose (ORC) and polyglactin 910 having dimensions (length, width) of 97.0 to 102.5 mm and a thickness of 1.40 to 2.50 mm was prepared as follows. Poly (glycolide-co-lactide) (PGL, 90/10 mol/mol) was melt-spun into fiber. A 80 denier multifilament yarn was consolidated into a 800 denier consolidated yarn. The consolidated yarn was crimped at approximately 110° C. The crimped yarn was cut into staple having a length of about 1.25". 20 g of the crimped staple was accurately weighed and laid out uniformly on the feed conveyor belt of a multi-roller carding machine. The environmental conditions (temp: 21° C./55% RH) were controlled. The staple was then carded to create a nonwoven batt. The batt was removed from the pick-up roller and cut into 4 equal parts. These were re-fed into the carder perpendicular to the collection direction. After this second pass the batt was weighed (19.8 g: 99% fabric yield) and then compacted into a felt. The compact felt was precisely laid onto an ORC fabric and firmly attached via 2 passes in the needlepunching equipment. The multilayered fabric was trimmed and scoured in 3 discrete isopropyl alcohol baths to remove spin finish and any machine oils. The scoured multilayered fabric was dried in an oven at 70° C. for 30 minutes, cooled and weighed. The water content was not more than 2.0% w/w Method of Impregnation Machine The Fibroline SL-Preg laboratory machine moves particles between electrodes by applying voltages up to 40 kV at frequencies of up to 200 Hz for a period of up to 60 seconds. The two electrode plates have a size of about 50×40 cm. The top plate is grounded.

The following standard settings were used: 40 kV, 100 Hz, 20-30 seconds.

Arrays

Powders were dosed gravimetrically into a 3D printed PMMA array after the array had been mounted onto the bottom electrode plate. The array was filled with reactive polymer powders using a scraping carton or metal spatula. The array measured 50×75×4 mm and contained 22×33=726 square wells (inner dimensions of each well: 2×2×2 mm). The combined volume of the 726 wells was approximately 5.8 mL.

Spacers

A spacer mask was placed on top of the array. The spacer was used to allow particles to move up and down when subjected to the alternating electric field. If no spacer is used, penetration and distribution through the carrier is limited.

For different substrates, different spacer heights are required. For TUFT-IT and SNoW this was a mask of 3 mm. This results in 3+4 mm=7 mm distance of the electrodes. For NU-KNIT/SNoW-Hybrid this was a mask of 1.5 mm. This results in 1.5+4 mm=5.5 mm distance of the electrodes Bleeding Experiments Standardized ex-vivo and in-vivo porcine bleeding models were used to assess haemostatic efficacy. All models use heparin to increase clotting time of blood to about 2 to 3 times activated coagulation time (ACT).

Ex-vivo model: live ex-vivo pig model with a fresh liver, perfused with heparinized fresh blood from the slaughterhouse to mimic real in-vivo situations a closely as possible. Livers are mounted onto a perfusion machine by which oxygenation, pH of blood, temperature and blood pressure are kept within vivo boundaries. Two livers and 10 litres of heparinized blood (5000 units/L) are collected at the slaughterhouse. Livers are transported on ice; blood at ambient temperature. Within two hours after collection, livers are inspected for lesions which are closed with gloves and cyanoacrylate glue.

Perfusion parameters: flow 600 ml/min; pressure 10-12 mmHg; temperature 37° C. (+/−1° C.); carbogen 0.25 litres a minute With a flat, round, rotating abrasion tool a circular bleeding wound (8 mm diameter) is created on the liver surface, with a rubber onlay so that the depth of the punched bleeding is always 3 mm After the liver is perfused properly (colour and temperature checked) samples are tested according to the following procedure: cut sample to the right size (2.7 by 2.7 cm); camera on; site number on camera; biopsy punch 8 mm; cut away biopt; remove blood from bleeding with gauze (2×); collect blood for 30 sec in pre-weight gauze; score bleeding (by 2 researchers); put sample on bleeding by a pre-wetted gauze (saline) and hold with little pressure for 1 min; observe for 5 min (check and score adhesion and haemostasis) and repeat after 30 minutes.

Porcine in-vivo model: standardized combined penetrating spleen rupture is inflicted in anesthetized swine (Domestic Pig, Female, Body Weight Range: 40 kg, Adult). A midline laparotomy is performed to access the spleen and other organs. Several types of surgical procedures were executed when using this model:

Using a circular biopsy punch, subcapsular standardized lesions (0.8 mm diameter) are made in liver and/or spleen. Test articles of approximately 2×2 cm are used in order to cover the injuries and manual tamponade is applied.

Using a scalpel, subcapsular standardized lesions are made in liver and/or spleen. The edge of the desired liver lobe or spleen is resected using a standard technique leaving the cut cross-section surface exposed. Test articles of 7.5×5 cm or 10×5 cm are used in order to cover the resection surfaces and manual tamponade is applied.

The right and left kidneys are identified and isolated using a combination of blunt and sharp dissection. The right and left kidney are dissected to allow grasping of the kidney with one hand and the caudal pole (approximately 2.5±1 cm diameter by 1±0.5 cm depth) of the kidney is amputated in a guillotine fashion with a scalpel. The target application site is aspirated and wiped clear of blood immediately before applying the test article to the actively bleeding site. Test articles of 7.5×5 cm or 10×5 cm are used in order to cover the resection surfaces and manual tamponade is applied. Same procedure is repeated in the cranial pole of the kidney.

Rat in-vivo model: 100 male Wistar (WU) rats are used of a body range weight of 270-300 gram. All rats are treated at least fifteen minutes prior to surgery with 0.02 mg/kg buprenofine subcutaneous. Induction anesthesia is given by inhalation of 5% isoflurane in an 1:1 mix of pressurized air and oxygen in an induction chamber. Maintenance dose is 3.5% isoflurane (also in 1:1 mix of pressurized air and oxygen) given through a snout mask. Rats are prepared by shaving, skin disinfection with iodine and sterile covers. The rats are fixated on a 15 degree tilted table with head higher then tail (murakimi 2008). Body temperature is kept at 38° C. with a heating pad and lamp, and then operated on through a 4-5-cm midline laparotomy using strict aseptic technique. The abdomen is opened by an abdominal midline incision, and the left lateral liver lobe is isolated. The lobe is placed on a firm piece of paper and the resection is made. The distal part of the liver lobe is excised with a scalpel, approximately 3 mm from the edge. A piece of patch (15 mm by 25 mm) is gently applied around the wound on the left lateral liver lobe, followed by applying manual tamponade with a wet gauze during 1 minute. Then the right part of the median liver lobe is prepared, a partial resection is made and a second patch of the same dimensions is applied in the same way.

Throughout all the ex-vivo and in-vivo procedures here described, the haemostatic products are applied with gentle pressure by a pre-wetted gauze (saline) and held for 1 min. After application of the product coagulation and adhesion to tissue are scored.

Scoring System for Patches: Coagulation
++++ Achieved immediately after tamponade
+++ Achieved <10 seconds after tamponade
++ Achieved <30 seconds after tamponade
+ Achieved within 3 minutes after tamponade
+/− Achieved after 3 minutes, second tamponade applied
− Not achieved Scoring System for Patches: Adhesion 10 Minutes after Application
++++ Very strong adhesion (patch breaks when being removed)+
++ Strong adhesion (patch breaks when being removed)+
+ Strong adhesion (patch can be removed without breaking)
+ Moderate adhesion (patch can be removed without breaking)+
+/− Mild adhesion (patch can be removed without breaking)
− Not achieved Example 1

Impregnation of Tuft-It with 70 μm NHS-POx or 35 μm dyed NHS-POx

Impregnation of Tuft-It with 70 μm NHS-POx (n=186)
Average weight of the non-impregnated Tuft-It was 0.74 g Average impregnation was 0.93 g, corresponding to an overall impregnation efficiency of about 56%

$$\left(\text{impregnation efficiency} = 100\% \times \frac{\text{impregnation weight}}{\text{weight of impregnated sheet}}\right)$$

Average loss was 8.9% w/w taking into account that 34% of NHS-POx was recovered from the arrays and re-used for impregnation.

No correlation was observed between the weight of the non-impregnated sheets and the level of impregnation (in grams)

Impregnation of a Double Tuft-It with 35 μm Blue NHS-POx (n=26)
 Average weight of the non-impregnated Tuft-It was 1.55 g
 Average impregnation was 2.78 g, corresponding to an overall impregnation efficiency of about 64%
 Average loss was about 10% while no NHS-POx needed to be recovered from the arrays to be re-used for impregnation.

Again, no correlation was observed between the weight of the non-impregnated sheets and the level of impregnation (in grams)

Example 2

Impregnation of PEM with 50 μm or 35 μm Reactive NHS-POx/NU-POx
 Impregnation of PEM with 50 μm NHS-POx/NU-POx granulate (n=186)
  Average weight of the non-impregnated PEM was 0.71 g
  Average impregnation was 1.65 g, corresponding to an overall impregnation efficiency of about 70%
  Average loss was about 10% while no polymer needed to be recovered from the arrays to be re-used for impregnation.
  No correlation was observed between the weight of the non-impregnated sheets and the level of impregnation (in grams)
 Impregnation of PEM with 35 μm NHS-POx/NU-POx Granulate (n=20)
  Average weight of the non-impregnated PEM was 0.72 g
  Average impregnation was 1.53 g corresponding to an overall impregnation efficiency of about 68%
  Average loss was about 5% while no polymer needed to be recovered from the arrays to be re-used for impregnation.
  No correlation was observed between the weight of the non-impregnated sheets and the level of impregnation (in grams)

Example 3

Impregnation of NU-KNIT/SNoW-Hybrid with 50 μm or 35 μm reactive NHS-POx/NU-POx
Impregnation of NU-KNIT/SNoW-Hybrid with 50 μm NHS-POx/NU-POx Granulate (n=5)
 Average weight of the non-impregnated NU-KNIT/SNoW-Hybrid was 1.56 g
 Average impregnation was 3.47 g, corresponding to an overall impregnation efficiency of about 55%
 Average loss was about 10% while no polymer needed to be recovered from the arrays to be re-used for impregnation.
 No correlation was observed between the weight of the non-impregnated sheets and the level of impregnation (in grams)

Impregnation of NU-KNIT/SNoW-Hybrid with 35 μm NHS-POx/NU-POx Granulate (n=12)
 Average weight of the non-impregnated NU-KNIT/SNoW-Hybrid was 1.52 g
 Average impregnation was 2.87 g, corresponding to an overall impregnation efficiency of about 65%
 Average loss was about 5% while no polymer needed to be recovered from the arrays to be re-used for impregnation.
 No correlation was observed between the weight of the non-impregnated sheets and the level of impregnation (in grams)

Example 4

Impregnation of PEM with 40 μm NHS-POx/NU-POx/P188 (5 and 10%) Granules
5% P188:
 Average weight of the non-impregnated PEM was 1.04 g (n=11)
 Average impregnation was 2.50 g, corresponding to an overall impregnation efficiency of about 70%
10% P188
 Average weight of the non-impregnated PEM was 1.03 g (n=6)
 Average impregnation was 2.56 g, corresponding to an overall impregnation efficiency of about 71%
5% PEG 3000:
 Weight of the non-impregnated PEM was 0.96 g (n=1)
 Impregnation was 2.19 g, corresponding to an overall impregnation efficiency of about 70%
10% PEG 3000:
 Weight of the non-impregnated PEM was 1.02 g (n=1)
 Impregnation was 2.48 g, corresponding to an overall impregnation efficiency of about 71%
NHS-POx/NU-PEG:
 Weight of the non-impregnated PEM was 1.01 g (n=1)
 Impregnation was 1.47 g, corresponding to an overall impregnation efficiency of about 59%

Example 5

Impregnation of NU-KNIT/SNoW-Hybrid with 40 μm NHS-POx/NU-POx/P188 (1.5, 2.5, 3.5, 5 and 10%) Granules
1.5% P188:
 Average weight of the non-impregnated NU-KNIT/SNoW-Hybrid was 1.55 g (n=1)
 Average impregnation was 1.90 g, corresponding to an overall impregnation efficiency of about 55%
2.5% P188:
 Average weight of the non-impregnated NU-KNIT/SNoW-Hybrid was 1.53 g (n=1)
 Average impregnation was 1.77 g, corresponding to an overall impregnation efficiency of about 54%
3.5% P188:
 Average weight of the non-impregnated NU-KNIT/SNoW-Hybrid was 1.45 g (n=1)
 Average impregnation was 1.19 g, corresponding to an overall impregnation efficiency of about 45%
5% P188:
 Average weight of the non-impregnated NU-KNIT/SNoW-Hybrid was 1.52 g (n=12)

Average impregnation was 2.87 g, corresponding to an overall impregnation efficiency of about 65%

10% P188:
  Average weight of the non-impregnated NU-KNIT/SNoW-Hybrid was 1.52 g
  Average impregnation was 2.61 g, corresponding to an overall impregnation efficiency of about 63%

Example 6

Impregnation of PEM with 100 µm Reactive NHS-POx/Gelita Spon Granules
  Average weight of the non-impregnated PEM was 0.79 g (n=1)
  Average impregnation after 2 cycles (one of 20 seconds and one of 30 seconds) was 1.15 g, corresponding to an overall impregnation efficiency of about 60%

Granulate was fluffy, so a limited amount of granulate could be applied in the array. To achieve a reasonable impregnation efficiency (or loading-%) 2 cycles were needed.

Example 7

Tuft-It is made of 0.75 gram of gelatin fibres and is able to hold max. 1 gram of NHS-POx (see Example 1). In order to increase the loading capacity beyond 1 g NHS-POx, so called "Tuft-It-plus" was made from standard Tuft-It by evenly dispersing 0.5 gram of standard Gelita Spon between the n=8 layers.

Increasing the density of Tuft-It resulted in two main outcomes: [1] more bulk material to achieve better hemostasis+[2] increased ability to hold more NHS-POx for improved hemostasis.

The Tuft-It-plus was impregnated with 70 µm NHS-POx. Loading of NHS-POx could be increased to 1.5 g per carrier using double spacers (double masks of each 3 mm leading to 30+3+4 mm powder array thickness and a total height between electrodes of 10 mm).

Example 8

Bleeding experiments were carried out using the impregnated sheets described in Examples 1-7.

An overview of the samples tested in shown in Table 1.

TABLE 1

| Sample | Example | Sheet | Reactive polymer particles |
|---|---|---|---|
| 1a | 1 | Tuft It | 70 µm NHS-POx |
| 1b | 1 | Tuft It | 35 µm blue NHS-POx |
| 2a | 2 | PEM | 50 µm NHS-POx/NU-POx |
| 2b | 2 | PEM | 35 µm NHS-POx/NU-POx |
| 3a | 3 | NU-KNIT/SNoW-Hybrid | 50 µm NHS-POx/NU-POx |
| 3b | 3 | NU-KNIT/SNoW-Hybrid | 35 µm NHS-POx/NU-POx |
| 4a | 4 | PEM | 40 µm NHS-POx/NU-POx/P188 (5%) |
| 4b | 4 | PEM | 40 µm NHS-POx/NU-POx/P188 (10%) |
| 5a | 5 | NU-KNIT/SNoW-Hybrid | 40 µm NHS-POx/NU-POx/P188 (1.5%) |
| 5b | 5 | NU-KNIT/SNoW-Hybrid | 40 µm NHS-POx/NU-POx/P188 (2.5%) |
| 5c | 5 | NU-KNIT/SNoW-Hybrid | 40 µm NHS-POx/NU-POx/P188 (3.5%) |
| 5d | 5 | NU-KNIT/SNoW-Hybrid | 40 µm NHS-POx/NU-POx/P188 (5%) |
| 5e | 5 | NU-KNIT/SNoW-Hybrid | 40 µm NHS-POx/NU-POx/P188 (10%) |
| 6 | 6 | PEM | 100 µm NHS-POx/Gelita Spon |
| 7 | 7 | Tuft-It-plus | 70 µm NHS-POx |

The results of the bleeding tests are summarised in Tables 2 and 3 (NT=not tested).

TABLE 2

| | (non heparinised) | |
|---|---|---|
| | In vivo rat (liver) | |
| Sample | Coagulation | Adhesion |
| 1a | ++++ | ++++ |
| 2a | ++++ | + |
| 7 | ++++ | +++ |

TABLE 3

| | (heparinised) | | | | | |
|---|---|---|---|---|---|---|
| | In vivo or ex-vivo (*) porcine (liver) | | In vivo porcine (spleen) | | In vivo porcine (kidney) | |
| Sample | Coagulation | Adhesion | Coagulation | Adhesion | Coagulation | Adhesion |
| 1a | +++ | ++++ | ++ | ++++ | ++ | ++++ |
| 1b | ++++ | ++++ | ++++ | ++++ | ++++ | ++++ |
| 2a | ++++ | + | ++++ | + | ++++ | + |
| 2b | ++++ | + | ++++ | + | NT | NT |

TABLE 3-continued (heparinised)

| | In vivo or ex-vivo (*) porcine (liver) | | In vivo porcine (spleen) | | In vivo porcine (kidney) | |
|---|---|---|---|---|---|---|
| Sample | Coagulation | Adhesion | Coagulation | Adhesion | Coagulation | Adhesion |
| 3a | +++ | +++ | ++++ | ++ | ++++ | ++ |
| 3b | ++++ | ++++ | ++++ | +++ | ++++ | +++ |
| 4a | ++++ | + | ++++ | ++++ | ++++ | ++++ |
| 4b | ++++ | + | +++ | ++ | +++ | ++ |
| 5a | +(*) | +(*) | NT | NT | NT | NT |
| 5b | +(*) | ++(*) | ++++ | +++ | NT | NT |
| 5c | +(*) | ++(*) | ++++ | ++++ | NT | NT |
| 5d | ++++ | + | ++++ | ++++ | ++++ | ++++ |
| 5e | ++++ | + | +++ | ++ | NT | NT |
| 6 | NT | NT | ++ | + | NT | NT |
| 7 | ++++ | ++ | ++++ | ++ | ++++ | ++ |

Example 9

Experiments were conducted to determine the effect of NU-POx content of the reactive NHS-POx/NU-POx granulate on in-vivo performance of the haemostatic patch.

Method of Impregnation

Hemostatic patches (Gelita Tuft-It®; 50×75 mm, appr. 0.7 g) were impregnated with reactive NHS-POx/NU-POx granules made via acetone granulation in molar ratios of 1:0.10, 1:0.20 and 1:0.40, said molar ratio referring to the ratio of the number of NHS groups provided by NHS-POx to the number of amine groups provided by the NU-POx. The same hemostatic patches were also impregnated with reactive NHS-POx powder.

One gram of the granulate/powder was distributed throughout the patches using the Fibroline SL-Preg laboratory machine. Next, the hemostatic patches were fixated, dried and packed in alu-alu pouches containing 1 g of silica and vacuum sealed.

Machine

The Fibroline SL-Preg laboratory machine moves particles between electrodes by applying voltages up to 40 kV at frequencies of up to 200 Hz for a period of up to 60 seconds. The two electrode plates have a size of about 50×40 cm. The top plate is grounded.

The following standard settings were used: 40 kV, 100 Hz, 20 seconds.

Arrays

Powders were dosed gravimetrically into a 3D printed PMMA array after the array had been mounted onto the bottom electrode plate. The array was filled with reactive polymer powders using a scraping carton or metal spatula. The array measured 50×75×4 mm and contained 22×33=726 square wells (inner dimensions of each well: 2×2×2 mm). The combined volume of the 726 wells was approximately 5.8 mL.

Spacer

A spacer mask was placed on top of the array. The spacer was used to allow particles to move up and down when subjected to the alternating electric field. If no spacer is used, penetration and distribution through the carrier is limited. For TUFT-IT this was a mask of 3 mm. This results in 3+4 mm=7 mm distance of the electrodes.

The in vivo performance of haemostatic patches containing NHS-POx:NU-POx granulate (0, 10, 20 and 40 percent amine groups from NU-POx, the percentage being calculated on the basis of the number of NHS groups provided by the NHS-POx) or NHS-POx powder was evaluated in a non heparinised in-vivo porcine model. The details of the patches that were tested are shown in Table 4.

TABLE 4

| Patch | Molar % amine | NHS-POx:NU-POx (g/g) | Grams of granulate in patch |
|---|---|---|---|
| 1 | 10 | 1:0.12 | 1 |
| 2 | 20 | 1:0.25 | 1 |
| 3 | 40 | 1:0.48 | 1 |
| 4 | 0 | 1:0 | 1 |

In Vivo Tests

Tests were carried out on adult female domestic pigs (40-50 kg) No anticoagulation agent was applied. Patch performance was tested on both spleen and liver. The spleen or liver were located and externalized as needed as the testing period progressed and their natural humidity was kept by covering them with saline soaked sponges.

Different Types of Injuries were Created:
  Liver: Abrasions, biopsy punches and resections
  Spleen: Resections An appropriately sized section of the liver parenchyma was abraded/punched to cause moderate to severe bleeding. The liver abrasions were created by surgical scalpel and a template of 1×1 cm2 and the circular punches using a 8 mm circular biopsy punch. Liver and spleen resections were created using a surgical knife.

The patch was applied immediately after the tissue resection or scarification:
  2×2 cm pieces for the biopsy punches and abrasions
  Complete 7.5×5 cm patch for resections The tested patches were applied on the bleeding tissue and gently pressed down by compression using a pre-wet gauze with saline solution. Tamponade was applied for an initial period of 10 seconds followed by subsequent 30 seconds intervals up to a total of 5 minutes.

A TUFT-IT patch that had not been impregnated was used as a reference (referred to as TUFT-IT).

The results of the in vivo tests are summarised in Table 5.

TABLE 5

| | Average time to haemostasis (in seconds) | | | |
|---|---|---|---|---|
| | Liver abrasion | Liver punch | Liver resection | Spleen resection |
| Patch 1 | 10 | 10 | 10 | 10 |
| Patch 2 | 10 | 10 | 10 | 10 |

TABLE 5-continued

| | Average time to haemostasis (in seconds) | | | |
|---|---|---|---|---|
| | Liver abrasion | Liver punch | Liver resection | Spleen resection |
| Patch 3 | 10 | 10 | 10 | 80 |
| Patch 4 | 10 | 80 | 75 | 165 |
| TUFT-IT | 135 | 165 | 210 | 225 |

Patches 1 to 4 showed very strong tissue adhesion, whereas only mild adhesion was observed for the TUFT-IT patch.

Patches 1 and 2 showed no more than very limited swelling after application. Patches 3 to 4 showed more, but still acceptable, swelling.

Example 10

Hemostatic patches (Gelita Tuft-It®; 50×75 mm, appr. 0.7 g) were impregnated with either a solution of NHS-POx, NHS-POx powder or NHS-POx/NU-POx granulate. The NHS-POx/NU-POx granulate used was made via acetone granulation in a molar ratio of 1:0.20 (see Example 9).

A spraying solution containing NHS-POx was prepared by dissolving NHS-POx in a 1:1 mixture of isopropyl alcohol and dichloromethane (200 g/L). The patches were impregnated with 5 mL of this spraying solution using a glass laboratory sprayer and pressurized air in a single spraying cycle. The total amount of NHS-POx delivered in this way was 1 gram per patch. After impregnation the patches were allowed to dry inside an oven at 40° C. for 2 hours, following which they were stored in a desiccator for 2 days before being packing in alu-alu pouches containing 1 g of silica and vacuum sealing.

In addition, patches were impregnated with 1 gram of NHS-POx powder or 1 gram of the NHS-POx/NU-POx granulate using the procedure described in Example 9.

The performance of the patches so prepared was tested in triplicate in the ex vivo liver perfused model under mild (<20 mL/min) and severe bleeding (>50 mL/min) conditions. With a flat, round, rotating abrasion tool a circular bleeding wound (8 mm diameter) was created on the liver surface, with a rubber onlay so that the depth of the punched bleeding was always 3 mm. The results are shown in Table 6.

TABLE 6

| | Ex-vivo | | | |
|---|---|---|---|---|
| | Mild bleeding | | Severe bleeding | |
| Type of impregnation | Hemostatic capacity | Adhesive properties | Hemostatic capacity | Adhesive properties |
| NHS-POx/NU-POx granulate | ++++ | ++++ | ++++ | ++++ |
| NHS-POx powder | +++ | ++++ | + | ++++ |
| NHS-POx solution | − | +/− | not tested | not tested |

The invention claimed is:

1. A method of preparing a tissue-adhesive sheet, comprising:
    (a) providing a fibrous sheet comprising a three-dimensional interconnected interstitial space;
    (b) providing reactive polymer particles comprising a water-soluble electrophilic polymer carrying at least 3 reactive electrophilic groups that are capable of reacting with amine groups in blood to form covalent bonds;
    (c) placing the fibrous sheet and the reactive polymer particles between two electrodes;
    (d) simultaneously subjecting the fibrous sheet and the reactive polymer particles to an electric field of 0.1 to 40 kV/mm to impregnate the interconnected interstitial space of the fibrous sheet with the reactive polymer particles.

2. The method according to claim 1, wherein the tissue-adhesive sheet is bio-absorbable.

3. The method according to claim 1, wherein the fibres in the fibrous sheet have a mean diameter of 1-500 μm.

4. The method according to claim 1, wherein the reactive polymer particles have a volume weighted mean diameter in the range of 10-100 μm.

5. The method according to claim 1, wherein the fibrous sheet has a felt structure, a woven structure or a knitted structure.

6. The method according to claim 5, wherein the fibrous sheet has a felt structure.

7. The method according to claim 1, wherein the fibrous sheet has a non-compressed mean thickness of 0.5-25 mm.

8. The method according to claim 1, wherein the fibrous sheet has a non-compressed density of less than 200 mg/cm$^3$.

9. The method according to claim 1, wherein the fibrous sheet comprises at least 50 wt. % fibres comprising gelatin, collagen, cellulose, modified cellulose, carboxymethyldextran, PLGA, sodium hyaluronate/carboxy methylcellulose, polyvinyl alcohol, chitosan or a combination thereof.

10. The method according to claim 1, wherein method comprises impregnating the fibrous sheet with 5-90% reactive polymer particles, calculated by weight of fibrous sheet.

11. The method according to claim 1, wherein the reactive polymer particles comprise at least 10 wt. % of the water-soluble electrophilic polymer.

12. The method according to claim 1, wherein the water-soluble electrophilic polymer is selected from the group consisting of polyoxazolines, polyethylene glycols, polyvinylpyrrolidones, polyurethanes and combinations thereof.

13. The method according to claim 1, wherein the fibrous sheet and the reactive polymer particles are placed between a lower electrode and an upper electrode, the electrodes being electrically insulated from each other by a dielectric and connected to the respective poles of an AC generator so as to subject the fibrous sheet and the reactive polymer particles to the electric field.

14. The method according to claim 13, wherein the fibrous sheet and the reactive polymer particles are passed between the lower electrode and upper electrode while the fibrous sheet and the reactive polymer particles are subjected to the electric field.

15. The method according to claim 1, wherein the fibrous sheet is subjected to the electric field for at least 0.1 second.

* * * * *